(12) United States Patent
Denisov et al.

(10) Patent No.: US 10,717,661 B2
(45) Date of Patent: Jul. 21, 2020

(54) ANTISEPTIC FORMULATION AND ITS USE

(71) Applicant: OBSHCHESTVO S OGRANICHENNOY OTVETSTVENNOSTYU "NANOBIOTEKH", Moscow (RU)

(72) Inventors: Albert Nikolaevich Denisov, Barnaul (RU); Yuriy Andreevich Krutyakov, Moscow (RU); Aleksey Aleksandrovich Kudrinskiy, Moscow (RU); Pavel Mikhailovich Zherebin, Tulskaya obl. (RU); Aleksey Igorevich Klimov, Vologda (RU)

(73) Assignee: OBSHCHESTVO S ORGANICHENNOY OTVETSTVENNOSTYU "NANOBIOTEKH", Moscow (RU)

( * ) Notice: Subject to any disclaimer, the term of this patent is extended or adjusted under 35 U.S.C. 154(b) by 0 days.

(21) Appl. No.: 15/502,762

(22) PCT Filed: Aug. 19, 2014

(86) PCT No.: PCT/RU2014/000615
§ 371 (c)(1),
(2) Date: May 9, 2017

(87) PCT Pub. No.: WO2016/028183
PCT Pub. Date: Feb. 25, 2016

(65) Prior Publication Data
US 2017/0260070 A1    Sep. 14, 2017

(51) Int. Cl.
| C02F 1/50 | (2006.01) |
| B82Y 30/00 | (2011.01) |
| A61L 2/18 | (2006.01) |
| C02F 103/42 | (2006.01) |
| A61K 33/38 | (2006.01) |

(52) U.S. Cl.
CPC ........... *C02F 1/505* (2013.01); *A61K 33/38* (2013.01); *A61L 2/18* (2013.01); *B82Y 30/00* (2013.01); *C02F 1/50* (2013.01); *A61K 2800/5428* (2013.01); *C02F 2103/42* (2013.01)

(58) Field of Classification Search
CPC .. A61L 2/18; B82Y 30/00; C02F 1/50; A61K 33/38
See application file for complete search history.

(56) References Cited

U.S. PATENT DOCUMENTS

| 1,993,686 A | 5/1935 | Schulenburg | |
| 5,565,143 A * | 10/1996 | Chan | H01B 1/20 252/514 |
| 5,922,909 A * | 7/1999 | Joffre | C07C 227/06 562/553 |

FOREIGN PATENT DOCUMENTS

| JP | 2009-235058 | 10/2009 | |
| JP | 2009235058 A | * 10/2009 | |
| JP | 2011-225722 | 11/2011 | |
| JP | 2012036188 A | * 2/2012 | ............. A01N 59/16 |
| JP | 2012-153863 | 8/2012 | |
| RU | 2414912 | 3/2011 | |
| RU | 2419439 | 5/2011 | |
| RU | 2427380 | 8/2011 | |
| RU | 2465891 | 11/2012 | |
| WO | WO 2008/137632 | 11/2008 | |
| WO | WO 2014/104916 | 7/2014 | |

OTHER PUBLICATIONS

Seungwook Kim et al (Korean Chem Soc, 2010, vol. 31, pp. 2918-2922).*
Kim et al (Korean Chemical Society, 2010, vol. 31, pp. 2918-2922) (Year: 2010).*
JP-2012036188-A, Espacenet machine English translation, printed in Aug. 2019 (Year: 2019).*
JP-2009235058-A, Espacenet machine English translation, printed in Aug. 2019 (Year: 2019).*
Letter/Written Disclosure of the Information Disclosure Statement for the above-referenced application, mailed on Apr. 25, 2017, 2 pages.
Kim et al., "Facile Synthesis of Silver Chloride Nanocubes and Their Derivatives," Bull. Korean Chem. Soc. 31(10):2918-2922 (2010).
Machine generated English translation of Russian Patent No. RU2414912, published Mar. 27, 2011, accessed from Espacenet on Mar. 23, 2017, 15 pages.
Machine generated English translation of Russian Patent No. RU2419439, published May 27, 2011, accessed from Espacenet on Mar. 23, 2017, 11 pages.
Machine generated English translation of Russian Patent No. RU2427380, published Aug. 27, 2011, accessed from Espacenet on Mar. 23, 2017, 11 pages.
Machine generated English translation of International Patent Publication No. WO 2014/104916 published Jul. 3, 2014, accessed from Espacenet on Mar. 23, 2017, 13 pages.
Xu et al., "Facile synthesis of small Ag@AgCl nanoparticles via a vapor diffusion strategy and their highly efficient visible-light-driven photocatalytic performance," Catalysis Science and Technology 4:3615-3619 (2014).
International Search Report, dated May 28, 2015 in connection with International Patent Appplication No. PCT/RU2014/000615, 2 pages.
Written Opinion, dated May 28, 2015 in connection with International Patent Appplication No. PCT/RU2014/000615, 4 pages.

(Continued)

*Primary Examiner* — Mark V Stevens
(74) *Attorney, Agent, or Firm* — Nixon & Vanderhye P.C.

(57) ABSTRACT

This invention falls within the scope of sanitary and hygiene, and of antiseptic formulations in particular, including disinfectants intended for disinfection of water in swimming-pools and other artificial reservoirs, for sanitary and hygienic treatment of rooms, household equipment, furniture, household appliances and industrial equipment, as well as for disinfection of rinse and waste water. An antiseptic formulation contains nanosized particles containing both silver and silver chloride. An antiseptic formulation can additionally contain at least one amphoteric surface-active substance. In order to perform disinfection of water, nanosized particles containing silver and silver chloride are added into water at least once.

5 Claims, No Drawings

(56) References Cited

OTHER PUBLICATIONS

International Preliminary Report on Patentability, dated Feb. 21, 2017 in connection with International Patent Appplication No. PCT/RU2014/000615, 5 pages.

Krutyakov et al., "New frontiers in water purification: highly stable amphopolycarboxyglycinate-stabilized Ag—AgCl nanocomposite and its newly discovered potential" *J. Phys. D: Appl. Phys.*, vol. 49: 375501—9 pages (2016).

Bowen MA et al: "Highly stable and efficient Ag/AgCI core-shell sphere: Controllable synthesis, characterization, and photocatalytic application", Appl Catal B, vol. 130-131, Feb. 1, 2013, pp. 257-263.

Dong L. et al. In Situ Photoactivated AgCl/Ag Nanocomposites with Enhanced Visible Light Photocatalytic and Antibacterial Activity // Eur. J. Inorg. Chem. 2012, 3200-3208.

Gustavo F. De Paula et al. Physical and Chemical Characterization of Poly(hexamethylene biguanide) Hydrochloride // Polymers 2011, 3, 928-941; doi:10.3390/polym3020928.

Ryoji Yanai et al. Effects of Ionic and Surfactant Agents on the Antimicrobial Activity of Polyhexamethylene Biguanide // Eye & Contact Lens vol. 37, No. 2, Mar. 2011.

Xu H., Li H., Xia J., Yin S., Luo Z., Liu L., Xu L. One-pot synthesis of visible-light-driven plasmonic photocatalyst Ag/AgCl in ionic liquid.—ACS applied materials & interfaces, 2011, 3(1), 22. DOI: 10.1021/am100781n.

Zhu Y., Liu H., Yang L., Liu J. Study on the synthesis of Ag/AgCl nanoparticles and their photocatalytic properties.—Materials Research Bulletin, 2012, 47(11), 3452. DOI: 10.1016/j.materresbull.2012.07.005.

\* cited by examiner

ANTISEPTIC FORMULATION AND ITS USE

This application is the U.S. National Stage of International Application No. PCT/RU2014/000615, field 19 Aug. 2014.

This invention falls within the scope of sanitary and hygiene, in particular to antiseptic formulations, including disinfectants intended for disinfection of water in swimming-pools and other artificial reservoirs, for sanitary and hygienic treatment of rooms, household equipment, furniture, household appliances and industrial equipment, as well as for disinfection of rinse and waste water.

Antimicrobial formulations intended for disinfection of water in swimming-pools and other artificial reservoirs, as well as for sanitary and hygienic treatment of rooms and equipment are known in the prior art.

The U.S. patent Ser. No. 19/993,686 dated May 3, 1935, discloses a way to produce soap with antiseptic properties containing 0.5-1 mass percent of "silver subchloride", i.e. a substance with the following formula: $Ag_xCl$, where x=2. The soap proposed in the patent exhibits bactericidal activity and does not change color when exposed to light. However, low efficiency of antimicrobial effect and, thus, high content of silver are among the limitations of this soap.

The U.S. Pat. No. 2,414,912 dated Mar. 27, 2011, issued by the Russian Federation, discloses a disinfecting water solution that contains silver ions, distilled water, lactic acid and 33% water solution of hydrogen peroxide. This invention is intended for use in health care, food and pharmaceutical industries and at municipal enterprises for disinfection and preservation of drinking water, as well as for disinfection of swimming-pools. However, its short-term biocidal effect is a limitation of this formulation.

The application No. 2010134589 for issue of a patent of the Russian Federation discloses a method to further prolong effect of fungicide disinfection of surfaces of basins and utility rooms of swimming-pools, in which nanoparticles of silver in concentration of 167 ppm are applied to surfaces of facing ceramic tiles by treatment of tiles with water organic solution of nanosized silver particles for 40 to 50 hours at the temperature of 16-20° C. with their further rinsing with hydrocarbon, water alcohol mixture and distilled water for 30 min at the room temperature. However, biocidal effect of this formulation is insufficient, and this is a limitation of the formulation. Furthermore, such multi-stage method of treatment is rather complicated and labour-intensive.

Antimicrobial Formulations Based on Polyhexamethylene Guanidine Salts

as well as on the based on polyhexamethylene biguanide salts

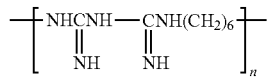

are known in the prior art.

The Patent of the Russian Federation No. 2427380 dated Aug. 27, 2011 discloses a disinfectant intended for treatment of skin covers, which contains colloidal silver, polyhexamethylene guanidine salt or polyhexamethylene biguanide salt. This disinfectant exhibits high biocide activity in respect of *Escherichia coli, Staphylococcus aureus, Leuconostoc mesenteroides, Aspergillus niger, Saccharomyces cerevisiae*. The minimal inhibitory concentration of the disinfectant disclosed in the Patent of the Russian Federation No. 2427380 in respect of these strains is several times less than the minimal inhibitory concentration of an analogous disinfectant, which does not contain colloidal silver. On the basis of the combination of the essential features, the disinfectant disclosed in the Patent of the Russian Federation No. 2427380 is the closest analogue of the present invention.

One of the main limitations of antimicrobial formulations based on colloidal silver and derivatives of polyhexamethylene guanidine that are available at the present moment, as well as limitations of relevant methods of use of these formulations is that positively charged particles of silver stabilized by derivatives of polyhexamethylene guanidine are easily sorbed in water-treatment filters, and especially in those made of materials containing silicon oxide and aluminosilicates, rather than in piping and walls of swimming-pools. Furthermore, these formulations lose stability at freezing and further melting. The rate of generation of silver ions that play a crucial part in bactericidal action of formulations based on colloidal silver, is rather low in the process of oxidative dissolution of silver particles and, thus, in order to maintain sufficient concentration of silver ions in water, it is required to use high concentrations of colloidal silver.

With regard to the aforesaid, there is a problem of increasing the efficacy of silver-bearing antiseptic formulations and relevant methods of their use, such as: a) a problem of increasing the stability of formulations by improving their resistance to freezing and further melting; b) a problem of reducing the degree of capturing of these formulations by water-treatment filters; c) a problem of increasing the rate of generation of silver ions and, therefore, of increasing bactericidal activity of disinfectants.

The technical results claimed are achieved by using the antiseptic formulation the details of which are described below.

DESCRIPTION OF THE INVENTION

In the process of experimental study of the influence of various additives for antimicrobial activity of formulations based on colloidal silver, it has been found that nanosized particles containing both silver and silver chloride (i.e. when one nanosized particle include both silver and silver chloride), including particles with nonstoichiometrical compound of $Ag_xCl$, where x>1, exhibits a higher level of antibacterial activity than analogous silver (Ag) particles and nanosized particles of silver chloride (AgCl).

It seems to be related to that fact that partial replacement of silver by silver chloride results to increasing of the rate of generation of silver ions by gradual dissolution of silver chloride. It allows to use a smaller amount of a formulation based on nanosized particles containing both silver and silver chloride to achieve the required efficacy of the bactericidal action than the amount of a formulation based on silver nanoparticles used for this purpose. Meanwhile, experimentally observed antibacterial activity of colloidal solutions of silver chloride nanosized particles is less than antimicrobial activity of formulations based on nanosized particles containing both silver and silver chloride. This phenomenon is due to that fact that, in the first instance, silver chloride colloidal solutions stabilized by low-molecular compounds are susceptible to aggregation, and especially when they exposed by electrolytes containing in biological media. The surface area of nanoparticle conglomerates is significantly less that the total surface area of particles forming a conglomerate and, thus, in the process of aggregation of silver chloride nanoparticles the rate of generation silver ions during dissolution of particles which varies in direct proportion to the surface area of particles, reduces significantly. Furthermore, when exposed to light silver chloride is readily susceptible to photolytic decomposition.

Thus, nanosized particles containing silver and silver chloride are characterized by: a) high rate of generation of silver ions due to presence of silver chloride; b) high aggregative stability characteristic of silver nanoparticles; and, therefore, c) significant antibacterial activity.

Depending on conditions of treatment and ingredients of the formulation, the use of nanosized particles containing both silver and silver chloride allows: a) to achieve the same or increased intensity of antimicrobial action at reduced concentration of the active substance and, therefore, at lower cost of an antiseptic formulation in comparison with formulations based on nanosized particles of silver or silver chloride; b) to increase the intensity of antimicrobial action compared to the intensity of action of silver colloid solution while the cost of the formulation remains unchanged; c) to increase the intensity of antimicrobial action compared to intensity of action of silver chloride colloid solution while the cost of the formulation remains unchanged.

In an experimental study of the influence of a stabilizer for the antimicrobial activity of formulations based on nanosized particles containing both silver and silver chloride, it has been found that formulations containing amphoteric surface-active substances (SAS), such as derivatives of w-aminocarboxylic acids and iminodicarboxylic acids, including N-alkyl-substituted derivatives of aminoacetic acid, 3-aminopropionic acid, iminodiacetic acid and iminodipropionic acid, are characterized by the highest aggregative stability.

In experimental studies, it has been found that such nanoparticles exhibit significant biocidal activity with respect to many prokaryotic and eukaryotic microorganisms, including gram-positive and gram-negative bacteria and fungi. It has been found that nanoparticles containing silver and silver chloride stabilized by amphoteric SAS are stable within a wide range of pH and are resistant to aggregation in the presence of electrolytes and due to this fact such nanoparticles can be used as antiseptic formulations with broad range of activity.

Nanoparticles containing both silver and silver chloride stabilized by tested amphoteric SAS are charged negatively and due to this, sorption of such nanoparticles is impeded in water-treatment filters that are charged similarly, and in filters made of materials containing silicon oxide and aluminosilicates in particular. Furthermore, colloid solutions of such nanoparticles retain aggregative stability at multifold freezing with further melting.

Nanoparticles containing both silver and silver chloride can be obtained, for example, by partial oxidation of nanosized silver particles in the presence of chloride ions.

The present invention relates to antiseptic formulations containing nanosized particles of both silver and silver chloride (i.e. when one nanosized particle include both silver and silver chloride).

In the preferred embodiment of the invention, an antiseptic formulation contains at least one additional amphoteric surface-active substance.

In the preferred embodiment of the invention, the concentration of an amphoteric surface-active substance in an antiseptic formulation is from 0.001 mass percent to 20 mass percent.

In the preferred embodiment of the invention, the concentration of nanosized silver particles in an antiseptic formulation is from $10^{-4}$ mass percent to 0.5 mass percent.

In the preferred embodiment of the invention, an antiseptic formulation contains supplemental additives.

In the preferred embodiment of the invention, supplemental additives are selected from a group comprising acidity correctors, corrosion inhibitors and thickeners.

In the preferred embodiment of the invention, at least one amphoteric surface-active substance is selected from a group comprising carboxylic acids and their derivatives with the following common formula:

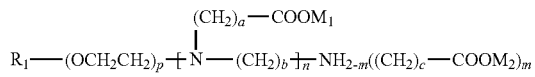

(type I compounds);
and carboxylic acids and their derivatives with the following common formula:

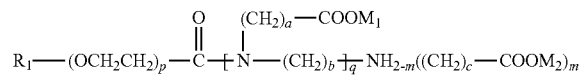

(type II compounds),
where $M_1$ and $M_2$ are selected from a group comprising H, Na, K, $NH_4$, where a equals 1 or 2, b equals 2 or 3, c equals 1 or 2, m equals 1 or 2, n equals or is greater than 0, p equals or is greater than 0, q is greater than 0, while substituent $R_1$ is selected from a group comprising branched and unbranched saturated and unsaturated linear and cyclic hydrocarbon radicals.

In the preferred embodiment of the invention at least one amphoteric surface-active substance is selected from a group comprising N-(2-ethylhexyl)-iminodipropionic acid and its salts, N-octyliminodipropionic acid and its salts, N-tallowalkyliminodipropionic acid and its salts, N-cocoalkyliminodipropionic acid and its salts, N-cocoalkylaminopropionic acid and its salts, a compound of the type I, where $R_i$ is defined as cocoalkyl, $M_1$ and $M_2$ are defined as Na, a=2, b=3, c=2, m=2, n=1, p=0; a compound of the type I, where $R_i$ is defined as cocoalkyl, $M_1$ and $M_2$ are defined as Na, a=2, b=2, c=2, m=2, n=1, p=0; a mixture of compounds of the type I, where $R_1$ is defined as cocoalkyl and $M_2$ are defined as Na, a=1, b=3, c=1, m=2, n falls within the range from 5 to 10, p=0; a mixture of compounds of the type I, where $R_1$ is defined as tallowalkyl, $M_1$ and $M_2$ are defined as Na, a=1, b=3, c 1, m=2, n falls within the range from 1 to 5, p=0; a mixture of compounds of the type I, where $R_1$ is defined as cocoalkyl, $M_1$ and $M_2$ are defined as Na, a=1, b=3, c=1, m=2, n falls within the range from 1 to 5, p falls within the range from 7 to 10; a compound of the type II, where $R_1$ is defined as cocoalkyl, $M_1$ and $M_2$ are defined as Na, a=2, b=3, c=2, m=2, q=1, p=0; a compound of the type II, where $R_1$ is defined as cocoalkyl, $M_1$ and $M_2$ are defined as Na, a=1, b=2, c=1, m=1, q=1, p=0; a mixture of compounds of the type II, where $R_1$ is defined as cocoalkyl, $M_1$ and $M_2$ are defined as Na, a=1, b=3, c=1, m=2, q falls within the range from 5 to 10, p falls within the range from 7 to 10.

The term "cocoalkyl" means a mixture of saturated and unsaturated hydrocarbon radicals, $C_8$-$C_{22}$ predominantly, which is a part of products obtained in the process of chemical treatment of coconut oil.

The term "tallowalkyl" means a mixture of saturated and unsaturated hydrocarbon radicals, $C_8$-$C_{24}$ predominantly, which is a part of products obtained in the process of chemical treatment of tallow oil.

The present invention also relates to methods of disinfection of water in which nanosized particles containing both silver and silver chloride are at least once added into water.

In the preferred embodiment of the invention, at least one amphoteric surface-active substance is further added into water.

In the preferred embodiment of the invention at least one amphoteric surface-active substance is selected from a group comprising carboxylic acids and their derivatives with the following common formula:

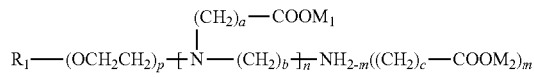

(type I compounds);
and carboxylic acids and their derivatives with the following common formula:

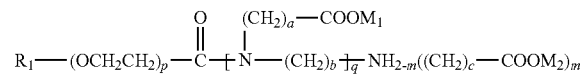

(type II compounds),
where $M_1$ and $M_2$ are selected from a group comprising H, Na, K, $NH_4$, where a equals 1 or 2, b equals 2 or 3, c equals 1 or 2, m equals 1 or 2, n equals or is greater than 0, p equals or is greater than 0, q is greater than 0, while substituent $R_1$ is selected from a group comprising branched and unbranched saturated and unsaturated linear and cyclic hydrocarbon radicals.

In the preferred embodiment of the invention at least one amphoteric surface-active substance is selected from a group comprising N-(2-ethylhexyl)-iminodipropionic acid and its salts, N-octyliminodipropionic acid and its salts, N-tallowalkyliminodipropionic acid and its salts, N-cocoalkyliminodipropionic acid and its salts, N-cocoalkylaminopropionic acid and its salts, a compound of the type I, where $R_1$ is defined as cocoalkyl, $M_1$ and $M_2$ are defined as Na, a=2, b=3, c=2, m=2, n=1, p=0; a compound of the type I, where $R_1$ is defined as cocoalkyl, $M_1$ and $M_2$ are defined as Na, a=2, b=2, c=2, m=2, n=1, p=0; a mixture of compounds of the type I, where $R_1$ is defined as cocoalkyl, $M_1$ and $M_2$ are defined as Na, a=1, b=3, c=1, m=2, n falls within the range from 5 to 10, p=0; a mixture of compounds of the type I, where $R_1$ is defined as tallowalkyl, $M_1$ and $M_2$ are defined as Na, a=1, b=3, c=1, m=2, n falls within the range from 1 to 5, p=0; a mixture of compounds of the type I, where $R_1$ is defined as cocoalkyl, $M_1$ and $M_2$ are defined as Na, a=1, b=3, c=1, m=2, n falls within the range from 1 to 5, p falls within the range from 7 to 10; a compound of the type II, where $R_1$ is defined as cocoalkyl, $M_1$ and $M_2$ are defined as Na, a=2, b=3, c=2, m=2, q=1, p=0; a compound of the type II, where $R_1$ is defined as cocoalkyl, $M_1$ and $M_2$ are defined as Na, a=1, b=2, c=1, m=1, q=1, p=0; a mixture of compounds of the type II, where $R_1$ is defined as cocoalkyl, $M_1$ and $M_2$ are defined as Na, a=1, b=3, c=1, m=2, q falls within the range from 5 to 10, p falls within the range from 7 to 10.

In the preferred embodiment of the invention, supplemental additives are further added into water.

In the preferred embodiment of the invention, supplemental additives are selected from a group comprising acidity correctors, corrosion inhibitors and thickeners.

The invention is illustrated with examples of alternative embodiments given below.

Example 1

A solution generated from partial oxidation of silver nanoparticles in colloidal solution containing 0.03 mass percent of amphoteric SAS sodium N-cocoalkyliminodipropionate and 0.0025 mass percent of nanosized silver particles was used as an antiseptic formulation. The colloidal solution of silver was obtained using a method disclosed in the Patent of the Russian Federation No. 2 419 439 dated May 27, 2011 "Antibacterial formulation and a method of its production", in this purpose solution of amphoteric SAS sodium N-cocoalkyliminodipropionate was used instead of solution of cationic SAS. Water solution of silver acetate was dropwise added into solution of amphoteric SAS under stirring. The mixture obtained was stirred for 15 minutes, and then water solution containing sodium borohydride $NaBH_4$ and the amphoteric SAS was dropwise added into the mixture under stirring. When the whole amount of sodium borohydride was added, the solution was further stirred for 1 hour. Thus, silver colloid solution of intense brown color was obtained. It was shown that during the process of synthesis, silver salt has been fully reduced by sodium borohydride with generation of nanosized silver particles. For the purpose of partial oxidation of silver nanoparticles, an excess of sodium chloride solution of double stoichiometric amount was added to the solution obtained and, then, hydrogen peroxide solution with concentration of 9 mass percent was dropwise added under stirring, at that the solution gradually gained intense violet-blue color.

In contrast to silver chloride colloidal solutions, the obtained antiseptic formulation A-1 is stable when exposed to light and exhibits long-term aggregate stability. At the same time, absorption spectrum of the obtained antiseptic formulation within the ultraviolet and visible regions of the spectrum differs from the absorption spectrum of the initial nanosized silver particles. The A-1 antiseptic formulation was studied using the method of translucent electron microscopy. In a sample of the formulation amorphous nanoparticles were found, of which silver particles were generated under decomposition by an electron beam. Generation of silver particles in the process of decomposition of the formulation was confirmed by information obtained by electron microdiffraction, since location of diffraction rings in the microdiffractogram pattern was the same as a standard microdiffractogram pattern of a polycrystal silver sample. Presence of silver chloride and silver in the nanoparticles of the A-1 formulation was further confirmed using the method of extended X-ray absorption fine structure spectroscopy (EXAFS). In a sample of coagulated nanosized particles of the A-1 formulation bonds Ag—Ag and Ag—Cl were detected giving evidence to that fact that nanosized particles of the formulation contained both silver and silver chloride.

Thus, in addition to sodium N-cocoalkyliminodipropionate, nanosized particles containing silver and silver chloride and other reaction products, the A-1 antiseptic formulation contained water of up to 100 mass percent.

In the process of evaluation of antibacterial activity of the formulation (with regard to bacteria of gram-negative bacteria *Escherichia coli* ATCC 25922 and gram-positive bacteria *Staphylococcus aureus* FDA 209P, as well as other bacteria), after incubation of cell suspension with colloidal solution of nanoparticles during 1 hour at the temperature of 30° C., samples of the suspension were taken and seeded to a solid agarized medium in Petri dishes. The Petri dishes were incubated for 24 hours at the temperature of 30° C. and the numbers of colonies grown were counted visually. Antibacterial activity of the control No. 1, an initial solution of silver nanoparticles stabilized by sodium N-cocoalkyliminodipropionate, and the control No. 2, colloidal silver chloride solution containing 0.03 mass percent of sodium N-cocoalkyliminodipropionate and 0.0025 mass percent of silver chloride, were estimated in an analogous way. The control No. 2 was produced by mixing stoichiometric amounts of silver nitrate and sodium chloride solutions which additionally contained sodium N-cocoalkyliminodipropionate.

It was shown that in order to achieve similar efficacy of antibacterial action, the control No. 1 was required to be added to the cell suspension in the amount of 2-2.5 times exceeding that of the proposed A-1 antiseptic formulation. Furthermore, it was shown that in order to achieve similar efficacy of antibacterial action, the control No. 2 was required to be added to the cell suspension in the amount of 7-8 times exceeding that of the proposed A-1 antiseptic formulation. It was also shown that to achieve similar efficacy of antibacterial action a mixture of equal amounts of controls No. 1 and No. 2 was required to be added to the cell suspension in the amount 4-5 times exceeding that of the proposed A-1 antiseptic formulation. This means that the antiseptic formulation based on nanoparticles containing silver and silver chloride exhibits more expressed biocidal activity than colloidal silver or colloidal silver chloride. This also means that use of nanoparticles containing silver and silver chloride results in synergetic effect of mutual enhancement of biocidal activity of silver and silver chloride. Thus, use of the proposed antiseptic formulation resulted in achievement of the technical result claimed, i.e. in increase in biocidal activity of the formulation.

Industrial and household equipment and appliances were treated with the A-1 antiseptic formulation obtained. Efficacy of antiseptic action of the formulation was evaluated on the basis of bacterial load of wipe sampling taken from the objects treated. It was shown that the antiseptic formulation obtained can be used for disinfection both in industry and households. The antiseptic formulation obtained can also be used for disinfection of water. It was shown that the antiseptic formulation obtained exhibits low toxicity for human, while not irritating skin and mucosa and not having sensitizing, carcinogenic, mutagenic or teratogenic effects.

After toxicology study had been carried out, the formulation obtained was tested as an antiseptic for disinfection of water in swimming-pools. To carry out the study, a basin of capacity of 10 $m^3$ was chosen. There was a standard recirculation circuit in the basin, including drain of water through a skimmer, filtration through a sand filter and refilling the basin with the water that had been filtered. Coagulation of weighted particles was performed 1 time a week by adding 60 g of aluminium sulfate. The basin was visited by 30 to 70 persons a day. For a month 6 liters of the antiseptic formulation obtained per 1 $m^3$ of water amounting to 15 mg of nanoparticles containing both silver and silver chloride were added to the basin daily. Concentration of silver in the water of the basin was determined daily with the method of absorption analysis using an atomic absorption spectrometer Shimadzu AA-7000 in accordance with a state standard of the Russian Federation GOST R 51309-99 "Drinking water. Determination of elements content by atomic spectrometry methods". It was shown that an average content of silver in water amounted to 4 $mg/m^3$ which was related to partial coagulation of particles of the formulation and their adsorption on filters. Maintaining such a silver concentration allowed achieving and maintaining the following values of bacterial load of water for the whole period of testing: total bacteria count (TBC) was not exceeding 40 colony-forming units (CFU) per ml; there were no coliform organisms; there were no thermotolerant coliform organisms; while all the aforesaid factors gave evidence to high efficacy of disinfection of water using the antiseptic formulation obtained.

The formulation obtained, therefore, can be used as an antiseptic for disinfection of water in swimming-pools.

Group of Examples 1

Antiseptic formulations of Group of examples 1 were obtained using a method analogous to that described in Example 1; in this case silver nitrate or silver acetate were reduced, while sodium N-cocoalkyliminodipropionate or sodium N-(2-ethylhexyl)-iminodipropionate, or sodium N-octyliminodipropionate, or N-tallowalkyliminodipropionate, or sodium N-cocoalkylaminopropionate, or a compound of the type I, where $R_1$ is defined as cocoalkyl, $M_1$ and $M_2$ stand for Na, a=2, b=3, c=2, m=2, n=1, p=0; or a compound of the type I, where $R_1$ is defined as cocoalkyl, $M_1$ and $M_2$ stand for Na, a=2, b=2, c=2, m=2, n=1, p=0; or a mixture of compounds of the type I, where $R_1$ is defined as cocoalkyl, $M_1$ and $M_2$ stand for Na, a=1, b=3, c=1, m=2, n falls within the range from 5 to 10, p=0; or a mixture of compounds of the type I, where $R_1$ is defined as tallowalkyl, $M_1$ and $M_2$ stand for Na, a=1, b=3, c=1, m=2, n falls within the range from 5 to 10, p=0; or a mixture of compounds of the type I, where $R_1$ is defined as cocoalkyl, $M_1$ and $M_2$ stand for Na, a=1, b=3, c=1, m=2, n falls within the range from 5 to 10, p falls within the range from 7 to 10; or a compound of the type II, where $R_1$ is defined as cocoalkyl, $M_1$ and $M_2$ stand for Na, a=2, b=3, c=2, m=2, q=1, p=0; or a compound of the type II, where $R_1$ is defined as cocoalkyl, $M_1$ and $M_2$ stand for Na, a=1, b=2, c=1, m=1, q=1, p=0; or a mixture of compounds of the type II, where $R_1$ is defined as cocoalkyl, $M_1$ and $M_2$ stand for Na, a=1, b=3, c=1, m=2, q falls within the range from 5 to 10, p falls within the range from 7 to 10 was used as an amphoteric SAS. Concentration of an amphoteric SAS was varied within the range from 0.001 mass percent to 20 mass percent; concentration of nanosized silver particles was varied within the range from $10^{-4}$ mass percent to 0.5 mass percent. In addition to amphoteric SAS, nanosized particles containing silver and silver chloride and products of reactions taking place during the process of synthesis of the formulation, each antiseptic formulation obtained contained water of up to 100 mass percent.

Evaluation of efficacy of the antiseptic formulations obtained was carried out with a method similar to that used in the Example 1 with regard to *Escherichia coli, Staphylococcus aureus, Leuconostoc mesenteroides, Legionella pneumophila, Shigella* spp., *Pseudomonas aeruginosa, Salmonella enterica, Candida albicans, Trichophyton* spp. The antiseptic formulations obtained exhibited expressed biocidal activity with regard to the microorganisms used in the study. In all cases the technical result was achieved which was a statistically significant increase in biocidal activity of the formulations as compared to analogous formulations based on nanosized silver particles and to those formulations based on silver chloride.

Industrial and household equipment and appliances were treated with the antiseptic formulations obtained. Efficacy of antiseptic action of the formulations was evaluated on the basis of bacterial load of wipe sampling taken from the objects treated. It was shown that the antiseptic formulations obtained can be used for disinfection both in industry and households. The antiseptic formulations obtained can also be used for disinfection of water.

It was shown that introduction of small amounts of chemically compatible supplemental additives to the composition of the antiseptic formulations developed, of acidity correctors, corrosion inhibitors and thickeners in particular, does not result in significant decrease in biocidal activity of the formulations.

It is obvious to skilled in the art that many antiseptic formulations based on nanoparticles containing both silver and silver chloride and amphoteric SAS that have not been mentioned in the examples hereof can be produced and used in a manner similar to that of producing the formulations described in the examples. It is obvious to skilled in the art that, if it is reasonable, technically realizable and legal, the claimed antiseptic formulations can be used to solve specific practical problems, like other antiseptic formulations. Thus, it is obvious that the list of the claimed methods of using antiseptic formulations does not limit possible embodiments of practical use of the claimed antiseptic formulations.

The invention claimed is:

1. An antiseptic formulation comprising:
   nanosized particles containing both silver and silver chloride, and
   at least one amphoteric surface-active substance,
   wherein at least one amphoteric surface-active substance is selected from among N-(2-ethylhexyl)-iminodipropionic acid and its salts, N-octyliminodipropionic acid and its salts, N-tallowalkyliminodipropionic acid and its salts, N-cocoalkyliminodipropionic acid and its salts, N-cocoalkylaminopropionic acid and its salts,
   a compound of a type I of the following formula:

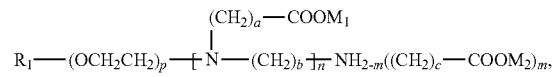

wherein $R_1$ is cocoalkyl, $M_1$ and $M_2$ are Na, a=2, b=2 or 3, c=2, m=2, n=1, p=0;
   a mixture of compounds of the type I, wherein $R_1$ is cocoalkyl, $M_1$ and $M_2$ are Na, a=1, b=3, c=1, m=2, n is within the range from 5 to 10, p=0; a mixture of compounds of the type I, where $R_1$ is tallowalkyl, $M_1$ and $M_2$ are Na, a=1, b=3, c=1, m=2, n is within the range from 1 to 5, p=0; a mixture of compounds of the type I, where $R_1$ is cocoalkyl, $M_1$ and $M_2$ are Na, a=1, b=3, c=1, m=2, n is within the range from 1 to 5, and p is within the range from 7 to 10;
   a compound of a type II of the following formula:

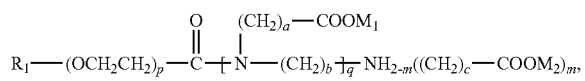

wherein $R_1$ is cocoalkyl, $M_1$ and $M_2$ are Na, a=2, b=3, c=2, m=2, q=1, p=0;
   or wherein $R_1$ is cocoalkyl, $M_1$ and $M_2$ are Na, a=1, b=2, c=1, m=1, q=1, p=0; and
   a mixture of compounds of the type II, wherein $R_1$ is cocoalkyl, $M_1$ and $M_2$ are Na, a=1, b=3, c=1, m=2, q is within the range from 5 to 10, p is within the range from 7 to 10.

2. The antiseptic formulation of claim 1 wherein the concentration of the amphoteric surface-active substance in the antiseptic formulation is within the range from 0.001 mass percent to 20 mass percent.

3. The antiseptic formulation according to claim 1, wherein the concentration of nanosized particles in the antiseptic formulation is within the range from $10^{-4}$ mass percent to 0.5 mass percent.

4. The antiseptic formulation of claim 1 wherein the antiseptic formulation contains supplemental additives.

5. The antiseptic formulation according to claim 4 wherein at least one of the supplemental additives is selected from the group consisting of acidity correctors, corrosion inhibitors and thickeners.

* * * * *